United States Patent
Bartels et al.

(10) Patent No.: US 12,186,478 B2
(45) Date of Patent: Jan. 7, 2025

(54) NOZZLE FIXTURE FOR AN INHALATION DEVICE

(71) Applicant: INVOX BELGIUM NV, Diepenbeek (BE)

(72) Inventors: Frank Bartels, Hattingen (DE); Jürgen Rawert, Cologne (DE)

(73) Assignee: INVOX BELGIUM NV, Diepenbeek (BE)

( * ) Notice: Subject to any disclaimer, the term of this patent is extended or adjusted under 35 U.S.C. 154(b) by 1178 days.

(21) Appl. No.: 16/766,752

(22) PCT Filed: Nov. 26, 2018

(86) PCT No.: PCT/EP2018/082581
§ 371 (c)(1),
(2) Date: May 26, 2020

(87) PCT Pub. No.: WO2019/102002
PCT Pub. Date: May 31, 2019

(65) Prior Publication Data
US 2021/0008298 A1    Jan. 14, 2021

Related U.S. Application Data

(60) Provisional application No. 62/591,027, filed on Nov. 27, 2017.

(30) Foreign Application Priority Data

Nov. 27, 2017 (EP) .................................... 17203883

(51) Int. Cl.
*A61M 11/00* (2006.01)
*B05B 1/02* (2006.01)

(52) U.S. Cl.
CPC ......... *A61M 11/007* (2014.02); *A61M 11/003* (2014.02); *B05B 1/02* (2013.01); *A61M 2205/19* (2013.01)

(58) Field of Classification Search
CPC  A61M 11/001; A61M 11/003; A61M 11/006; A61M 11/007; A61M 11/008;
(Continued)

(56) References Cited

U.S. PATENT DOCUMENTS

2004/0164173 A1    8/2004  Jarchau
2007/0282276 A1*  12/2007  Boeck ..................... F04B 53/16
                                                                              604/207

(Continued)

FOREIGN PATENT DOCUMENTS

DE    102004001451 A1    8/2005
EP         0627230 B1    2/2000
(Continued)

OTHER PUBLICATIONS

International Preliminary Report on Patentability for International Application No. PCT/EP2018/082581, mailed on Nov. 14, 2019, 13 pages.

(Continued)

*Primary Examiner* — Justine R Yu
*Assistant Examiner* — Matthew R Moon
(74) *Attorney, Agent, or Firm* — Synergy IP Group AG; Colin Jamieson

(57) ABSTRACT

The invention relates to the field of inhalation devices for liquids. In particular, the invention relates to a fixture for a nebulizing nozzle to be used in such an inhalation device. A nozzle fixing assembly (1) for an inhalation device, comprising an elastically deformable seal element (2), having a continuous opening (3) capable of receiving a nozzle body (4), said seal element (2) and said nozzle body (4) each (Continued)

having a high pressure side (2A, 4A) and an outlet side (2B, 4B); and a pressure element (5) with a high pressure side (5A), said side being arranged to face the high pressure side (2A) of the seal element (2); wherein (i) the high pressure side (2A) of the seal element (2) is substantially flat, and (ii) the high pressure side (5A) of the pressure element (5) is chamfered in a way that, in the assembled state, the distance between these high pressure sides (2A, 5A) is higher in a central region (C) than in a peripheral region (P).

12 Claims, 2 Drawing Sheets

(58) Field of Classification Search
CPC ........ A61M 2205/19; B05B 1/00; B05B 1/02; B05B 15/14; B05B 15/18
See application file for complete search history.

(56) References Cited

U.S. PATENT DOCUMENTS

| | | |
|---|---|---|
| 2010/0154792 A1 | 6/2010 | Geser et al. |
| 2012/0174919 A1* | 7/2012 | Hausmann ............. A61M 11/06 |
| | | 128/200.23 |
| 2017/0281880 A1 | 10/2017 | Van Egmond et al. |

FOREIGN PATENT DOCUMENTS

| | | |
|---|---|---|
| EP | 0853498 B1 | 3/2002 |
| EP | 2044967 A1 | 4/2009 |
| EP | 17168869 | 11/2018 |

OTHER PUBLICATIONS

Written Opinion of International Application No. PCT/EP2018/082581, mailed on Jan. 24, 2019, 6 pages.

* cited by examiner (not claimed)

NOZZLE FIXTURE FOR AN INHALATION DEVICE

CROSS REFERENCE TO RELATED APPLICATIONS

This application is a United States National Stage Application filed under 35 U.S.C. § 371 claiming priority to and the benefit of PCT Application No. PCT/EP2018/082581, filed on Nov. 26, 2018, which claims priority to and the benefit of European Application No. 17203883.8, filed on Nov. 27, 2017, and U.S. Provisional Application Ser. No. 62/591,027, filed on Nov. 27, 2017, all of which are incorporated herein by reference in their entireties.

FIELD OF THE INVENTION

The invention relates to the field of inhalation devices for liquids. In particular, the invention relates to a fixture for a nebulizing nozzle to be used in such an inhalation device.

BACKGROUND OF THE INVENTION

Nebulizers or other aerosol generators for liquids are known from the art since a long time ago. Amongst others, such devices are used in medical science and therapy. There, they serve as inhalation devices for the application of active ingredients in the form of aerosols, i.e. small liquid droplets embedded in a gas. Such an inhalation device is known e.g. from document EP 0 627 230 B1. Essential components of this inhalation device are a reservoir in which the liquid that is to be aerosolized is contained; a pumping unit for generation of a pressure being sufficiently high for nebulizing; as well as an atomizing device in the form of a nozzle.

An improvement of such an inhalation device is disclosed in patent application EP 17168869, filed by the same applicant as the present invention, the content of which is incorporated herein in its entirety.

In order to achieve a sufficiently homogenous and fine mist of liquid droplets, usually, relatively high pressures such as 10 bar, up to 1000 bar, are necessary. In order to keep the amount of vaporized liquid for each dose acceptably low, the nebulizing nozzle comprises usually one or several channels, each having a cross section only in the order of several $\mu m^2$, e.g. from 2 $\mu m^2$ to 200 $\mu m^2$. The channels are present in a nozzle body, and are often fabricated using micro technological fabrication techniques such as micro etching, micro lithography and the like. However, these techniques are often targeted at hard and brittle materials such as silicon, glass or metal, and in order to avoid any undesired deformation of the nozzle body when being subjected to said high pressures, the nozzle body is often made from a very rigid material. However, this delicate and essential element of the entire device must be securely be fixed within the same. This involves liquid tightness as well as mechanical safety. Therefore the fixture of said nozzle body within the inhalation device demands special attention.

From document EP 0 853 498 B1, a nozzle fixture is known which comprises a pot shaped holder with a recess inside, and an elastomeric molding configured to fit into this recess. The molding itself has an opening designed to receive the nozzle body. When inserted into the recess, one of the surfaces of the molding (and the nozzle body) is exposed to the high pressure during use. The holder has a small orifice in its bottom which aligns with the nozzle outlet, and the matching walls of both the holder and the molding are frustum shaped.

According to more recent document DE 10 2004 001 451 A1 which was filed by the same applicant as EP 0 853 498 B1, the aforementioned solution works well for medium and high pressures, but provides insufficient tightness for low pressures of e.g. less 10 bar. Therefore, the latter document proposes a solution where said holder is complemented at the high pressure side with a counterpart closing the holder, said counterpart having a circumferential ridge, said ridge being designed to displace elastic material of said molding when being pressed against the same when assembled. Further, on its high pressure side, the molding is not flat, but has centrally a sloping recess, resulting in slants or chamfers which are inclined towards the centrally arranged nozzle body.

While the latter solution was claimed to result in an increased liquid tightness also at low pressures, the fabrication of said elastomeric molding becomes more complicated. Further, mounting said molding into the holder requires special attention, since the high and the low pressure sides are different from each other.

The object of the invention is to provide a device that avoids the drawbacks of the known art. In particular, the nozzle fixture should provide a sufficient liquid tightness within the entire typical pressure range of an inhalation device, and its parts should be easy to manufacture and to assemble.

DESCRIPTION OF THE INVENTION

The object is solved by a device according to claim 1. Advantageous embodiments are described in the respective dependent claims, the subsequent description, as well as the accompanying figures.

The nozzle fixing assembly serves for the use within an inhalation device. The device is used for generation of an aerosol of medically active liquids, and in particular, of such aerosols which can be inhaled.

In a further aspect, the invention relates to a medical inhaler or a nebulizer for medical fluids comprising a nozzle fixing assembly as described herein with all its embodiments.

The nozzle fixing assembly, or assembly in short, is adapted to be substantially pressure tight, which means that during normal use, despite the usually high pressures that are present upstream of the nozzle, no, or a very small neglectable leakage is desired. The nozzle fixing assembly is in particular adapted to be pressure tight, when a nozzle body is inserted.

The assembly comprises an elastically deformable seal element, having a continuous opening capable of receiving a nozzle body, wherein the seal element and the nozzle body each having a high pressure side and an outlet side. In other words, the seal element has an opening into which the nozzle body can be inserted. The opening is typically a through-hole connecting the high pressure side and the outlet side of the seal element. Preferably, the opening has a cross section which is slightly (e.g. 10 µm to 1 mm) larger than the cross section of the nozzle body, so that the latter can easily be inserted. The opening can have parallel walls, or it can have a slight wall angle, being more narrow at the outlet side of the nozzle body. In one embodiment, the opening has a longitudinal axis which is congruent with the longitudinal axis of the seal element. In some embodiments, the nozzle fixing assembly comprises a nozzle body.

In one embodiment, the nozzle is of a type that is used in so-called soft mist inhalers, and configured to emit at least two jets of liquid to be nebulized such as to collide and form an aerosol of dispersed liquid droplets in air. Such nozzles are adapted to function at relatively high pressure, such as in the range from about 10 bar to about 100 bar.

The nozzle body has a side which is, when the device is actuated, subjected to a high pressure of liquid (high pressure side). The liquid is pressed into one or several channels, optionally comprising filters or the like. The opposite end of the channel(s) ends in the actual nozzle outlet, where an inhalable mist is produced upon actuation of the device. This end is surrounded by ambient pressure, hence, this side is called the outlet, or low pressure side.

The seal element is made from, or comprises a layer of, elastically deformable material. Therefore, when subjected to high external pressure, the seal element can be deformed, and/or an interior stress is built up, resulting in pressures pointing outwards. In general, the external pressure can be the result of physical contact with another object, or of pressurized liquid touching a surface of the seal element. If the material of the seal element is substantially incompressible, the volume remains constant. Pressurizing one surface results in dilation of other surfaces. If the material is compressible, the volume is reduced upon pressurization, but still, the pressure is "transferred" throughout the material towards the other surfaces, which will dilate if the available space allows so, or build up a certain counter pressure if restrained.

Further, the assembly comprises a pressure element with a high pressure side, which may also be referred to as downstream side, said side being arranged to face the high pressure side of the seal element. The pressure element is situated opposite of the high pressure side of both the seal element and the nozzle body. The object of the pressure element is to apply pressure to the seal element. This can be done in various ways, with comparable results, which will be discussed in detail further below.

It is clear that the pressure element must be configured to allow the flow or bypass of the liquid to the nozzle to be vaporized. This can e.g. be achieved by means of a central opening in the pressure element, or a plurality of openings, that allow fluid communication between a liquid supply, e.g. from a reservoir arranged further upstream, and the space between pressure element and seal element (i.e. downstream of the pressure element).

Further, the high pressure side of the seal element is substantially flat, and this side lies in a plane being perpendicular to a longitudinal axis of the seal element.

According to the invention, the high pressure side of the pressure element is chamfered in a way that, in the assembled state, the distance between both high pressure sides is higher in a central region than in a peripheral region, provided there is no substantial deformation of the seal element. In other words, there exists a central region (i.e. a region which is closer to the longitudinal axis), and a peripheral region (i.e. a region which is further away from said longitudinal axis, therefore being closer to the ends or edges of the side). "Chamfered" means that the distance between the surface of the high pressure side and the high pressure side of the seal element decreases from the center to the corners or circumference of the surface. In the context of the present invention chamfered is used synonymous with inclined or sloped with respect to the surface of the high pressure element.

In a particular embodiment, the pressure element is chamfered in a way that, in the assembled state, the distance between the high-pressure side of the seal element and the pressure element is higher in a central region than in a peripheral region, wherein said central region corresponds to a region facing said continuous opening when following said longitudinal axis. In some embodiments, said central region is a region located towards the longitudinal axis of the seal element.

In the sense of the present invention chamfered or inclined or sloped means that the thickness of the pressure element is greater than in the central region, when the thickness us measured in the direction of the longitudinal axis.

In the assembled state, the chamfer may therefore result a space or void volume that has a greater height in the central region than in the border or peripheral regions. This shape, in turn, results in a permanent or temporary exertion of pressure in the periphery of the seal element's high pressure side. As a result, the seal element deforms and effectively seals towards the nozzle body, and preferably, to the other sides that rest against solids surfaces as well.

According to one embodiment, the assembly further comprises an (e.g. pot- or cup-shaped) holder with a recess, inside which the seal element, the nozzle body and the pressure element are arranged. In other words, the holder serves as a housing for the other elements. The holder comprises a low pressure surface which is, in the assembled state, in contact with the outlet side of the nozzle, i.e. the inside of a "front wall" which forms the "front side" where the atomized liquid leaves the assembly. The holder further comprises an inside contour matching an outside contour of the elastomeric molding, so that the gap between said contours becomes small, making it easier to be liquid tight. Further, the holder has a high pressure end, containing at least the high pressure side of the pressure element. The recess in the holder is arranged in such a way that the seal element (optionally with the nozzle accommodated within the opening in the seal element) is inserted into it from the holder's high pressure side. Typically, the seal element is fully inserted into the recess, and the pressure element may be partially or entirely be inserted into the holder. Its high pressure side points to the inside of the holder, and thus, towards the high pressure space.

This embodiment allows and advantageously convenient installation of the assembly into the device. Also, testing and replacing the assembly is easier to achieve.

In one embodiment, the recess has the shape of a truncated cone, which may also serve the purpose of ease of assembly. Optionally, the seal element may have a corresponding shape of a truncated cone.

In one embodiment, in the assembled state, the high pressure side of the pressure element is at least partially in physical contact with the high pressure side of the seal element. Mechanical pressure is exerted onto the high pressure side of the seal element, the element is deformed, and a permanent seal is provided (as long as the physical contact is not released). This solution gives good control over the amount of pressure that is exerted in order to form the seal. Further, remaining liquid stays inside the aforementioned space, even when the device is not actuated.

In one embodiment, said distance is, in the assembled state, zero at the peripheral region (or at least a portion of the peripheral region) and larger than zero at the central region. In other words, the high pressure side of the pressure element is in contact with the high pressure side of the seal element at the periphery, but not in the central region.

In another embodiment, in the assembled state, the high pressure side of the pressure element is spaced apart from the high pressure side of the seal element, such that no physical contact is established. In this embodiment, the sealing is effected by the deformation of the seal element which is the result of the concentration of the high pressure pulse inside the aforementioned space. Since the space has a greater height in the central region than in the border regions (periphery), the pressure pulse, as it occurs when actuating the device, forms an increasingly high pressure, the more narrow said space is. Therefore, from the center region to the periphery, the pressure which is exerted onto the high pressure side of the seal element increases. In other words, the pressure exerted onto the high pressure side of the seal element is not uniform, but stronger at the periphery. As a result, the seal is pressed towards the side walls of the nozzle body, sealing it tight. Further, a part of the pressure is distributed also towards the inside of the front wall mentioned above, thus also resulting in a sealing of the according surface, so that a possible bypass to the nozzle channel is blocked.

In one embodiment, in a cross section along the longitudinal axis, the chamfered surface has a linear shape. This means that the angle between the longitudinal axis (or the surface of the high pressure side of the seal element) and a line that goes from the center of the high pressure side of the pressure element to its periphery is substantially constant.

In another embodiment, said line follows a concave curve, i.e. a curve that has a steep angle at the periphery, and a flat angle in the center.

In yet another embodiment, said line follows a convex profile.

In one embodiment of the nozzle fixing assembly, the high pressure side of the pressure element is chamfered substantially in its entirety. This means that from the center, or more precisely, from the high pressure side edge of a possible opening that serves as a bypass to the pressure element, to the periphery, or more precisely, to the circumferential corner of the high pressure side of the pressure element, the respective surface is inclined with respect to the flat surface of the seal element.

In another embodiment, not the entire high pressure side of the pressure element consists of inclined or chamfered surfaces, but it has a central region which is substantially flat, i.e. parallel to the high pressure side of the seal element. Thus, the inner region of said side is substantially parallel to the aforementioned flat surface. However, since in the relevant regions, namely the peripheral ones, the aforementioned effect of the decreasing height of the space is present, the sealing effect occurs nevertheless.

In another embodiment, the pressure element serves as a closure of the holder's high pressure end, thus fulfilling the function of a closure or a lid. Hence, no additional part is needed in order to provide a compact assembly which is less susceptible to contamination than an open assembly.

In another embodiment, a separate lid is provided which can be attached to said high pressure end. The lid pushes against the upstream side of the pressure element and keeps the same in place with regard to the seal element. Depending on the respective construction, this can mean that the high pressure side of the pressure element is spaced apart from, or just touches, or physically presses against the high pressure side of the seal element (see above).

According to another embodiment, the nozzle fixing assembly further comprises a washer which is arranged between the two high pressure sides of seal element and pressure element, said washer having one or more continuous openings for fluidic connection of the high pressure space with the nozzle inlet. The opening(s) is (are) arranged at the high pressure side of the nozzle body, such that one or several according bypasses are provided for the liquid.

Generally speaking, the washer has the purpose of acting as a means for further control of the pressure exerted onto the high pressure side of the seal element.

The washer has a first side for contacting the high pressure side of the seal element, said first side being substantially flat, and an opposite second side which faces the high pressure side of the pressure element. In other words, the washer rests flat against the seal element, while the opposite side of the washer is not flat and points into the aforementioned space.

Said second side of the washer is chamfered in a way that, in the assembled state, the distance between its second side and the high pressure side of the seal element is higher in a central region than in a peripheral region. Thus, an interspace is provided between the second side of the washer and the high pressure side of the pressure element.

The interspace may be more narrow in its periphery than in its center.

In other words, the second side has a shape that, together with the opposing high pressure side of the pressure element, aforementioned space is somewhat reduced, but the remaining interspace still allows for the aforementioned physical effect of the pressure concentration.

At the same time, by adjusting the exact shape and size of the washer, the concrete influence on said effect can be precisely adjusted. This can be necessary when the device is adapted to atomize a different liquid, possibly having different fluidic properties. Thus, not the entire assembly, but only one component of the same must be altered in order to achieve again best sealing results.

In another embodiment, in a cross section along the longitudinal axis, the second surface of the washer has a profile resembling the negative of the profile of the chamfered surface of the pressure element. That means that the profile of the second side of the washer is a negative of the profile of the high pressure side of the pressure element. This results in partially parallel surfaces; however, in the peripheral region of the volume or interspace, the reduction of height of the space still exists, meaning that it is more shallow in these regions than in the more central regions.

In a particular embodiment, the invention relates to a Nozzle fixing assembly for an inhalation device, the assembly being adapted to hold a nozzle body substantially pressure tight when said nozzle body is inserted, comprising:
  an elastically deformable seal element, having
    a longitudinal axis;
    a continuous opening along said axis which is capable of receiving said nozzle body;
    a high pressure side having a surface;
    an outlet side;
  a pressure element with a high pressure side having a surface, said high pressure side being arranged to face the high pressure side of the seal element; wherein
  (i) the surface of the high pressure side of the seal element is substantially flat and lies in a plane perpendicular to the longitudinal axis of the seal element, and
  (ii) the surface of the high pressure side of the pressure element is chamfered or sloped in a way that, in the assembled state, the distance between the surface of the high pressure side of the seal element and the surface of the high pressure side of the pressure element is higher in a central region than in a peripheral region, wherein said central region is a region located towards the longitudinal axis of the seal element and said peripheral region is a region peripherally located with respect to the longitudinal axis of the seal element.

Optionally, the nozzle fixing assembly further comprises the nozzle body. In other words, in this embodiment, the nozzle body is already part of the assembly, and readily inserted into the aforementioned opening of the seal element. Preferably, the outlet side of the nozzle body is in line with the outlet side of the seal element, and/or the high pressure sides of bot elements are in line as well.

As explained, the invention overcomes the drawbacks of the known art. In particular, the nozzle fixture assembly provides a sufficient liquid tightness within the entire typical pressure range of an inhalation device, and its parts are easy to manufacture and to assemble. Furthermore, in one embodiment, the assembly allows for an enhanced control of the sealing pressure.

DESCRIPTION OF FIGURES

In FIG. 1, a schematic cross sectional view of a nozzle fixing assembly 1 with a seal element known from the art is shown.

Figure 1:
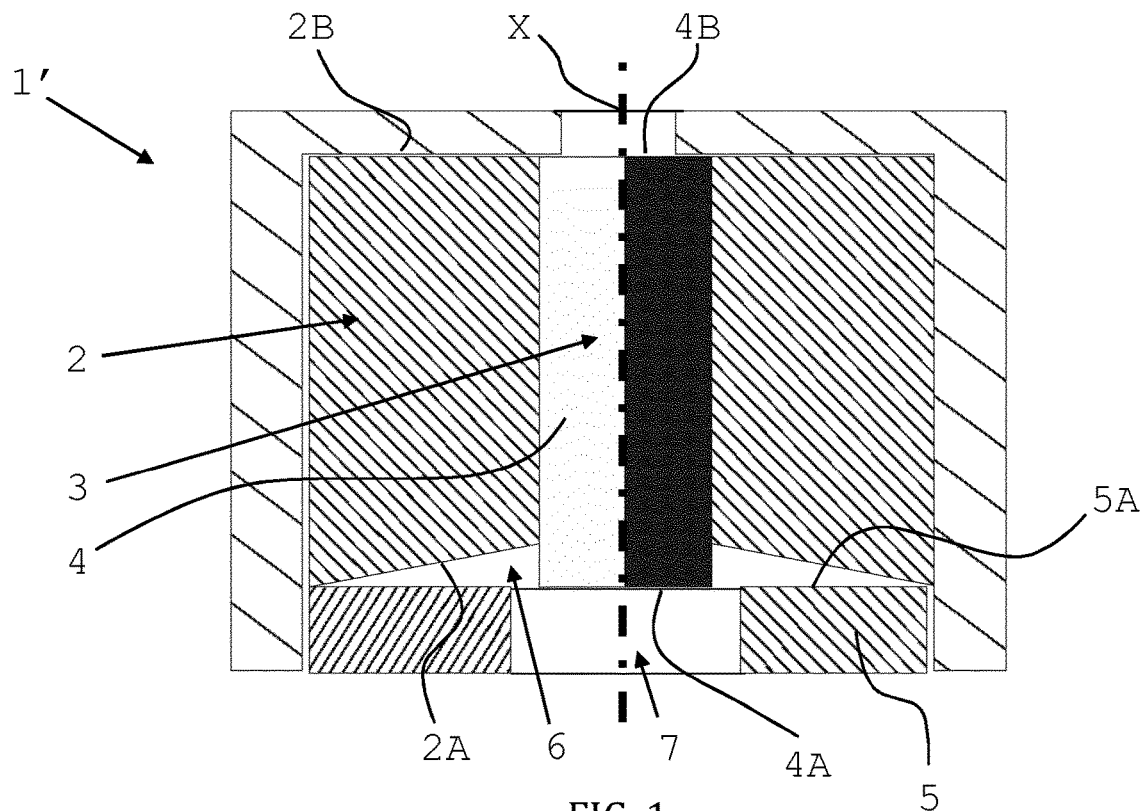
FIG. 1 shows a schematic cross sectional view of a nozzle fixing assembly known from the art.

A nozzle fixing assembly 1' comprises an elastically deformable seal element 2 which is known from the art. This seal element 2 has a continuous opening 3 into which a nozzle body 4 is inserted. The depicted nozzle body 4 consists of two halves, drawn in white and black. In the interface between these halves, channel structures are present (not depicted) which connect the upstream end (bottom of the picture) with the downstream end (top of the picture) of nozzle body 4.

Seal element 2 and nozzle body 4 each have a high pressure side 2A, 4A and an outlet side 2B, 4B.

Further, a pressure element 5 is present with a high pressure side 5A. This side 5A is arranged to face the high pressure side 2A of the seal element as well as the high pressure side 4A of the nozzle body 2. Between said sides 2A/4A and 5A, a space 6 is present which is temporarily loaded with high pressure liquid during actuation of the device (not depicted). Pressure element 5 is configured to allow bypass of the liquid to be vaporized into space 6. In the example, this is achieved by means of a central opening 7.

In the assembly 1, the high pressure side 2A of the seal element 2 is chamfered. Looking in direction of the longitudinal axis X (dash-dotted line), the individual surfaces of the high pressure side 2B of seal element 2 are all tilted towards this axis, and do not stand perpendicular to the same. At the same time, the high pressure side 5A of the pressure element 5 is flat, i.e. its surface is substantially perpendicular to said axis X.

Figure 2:
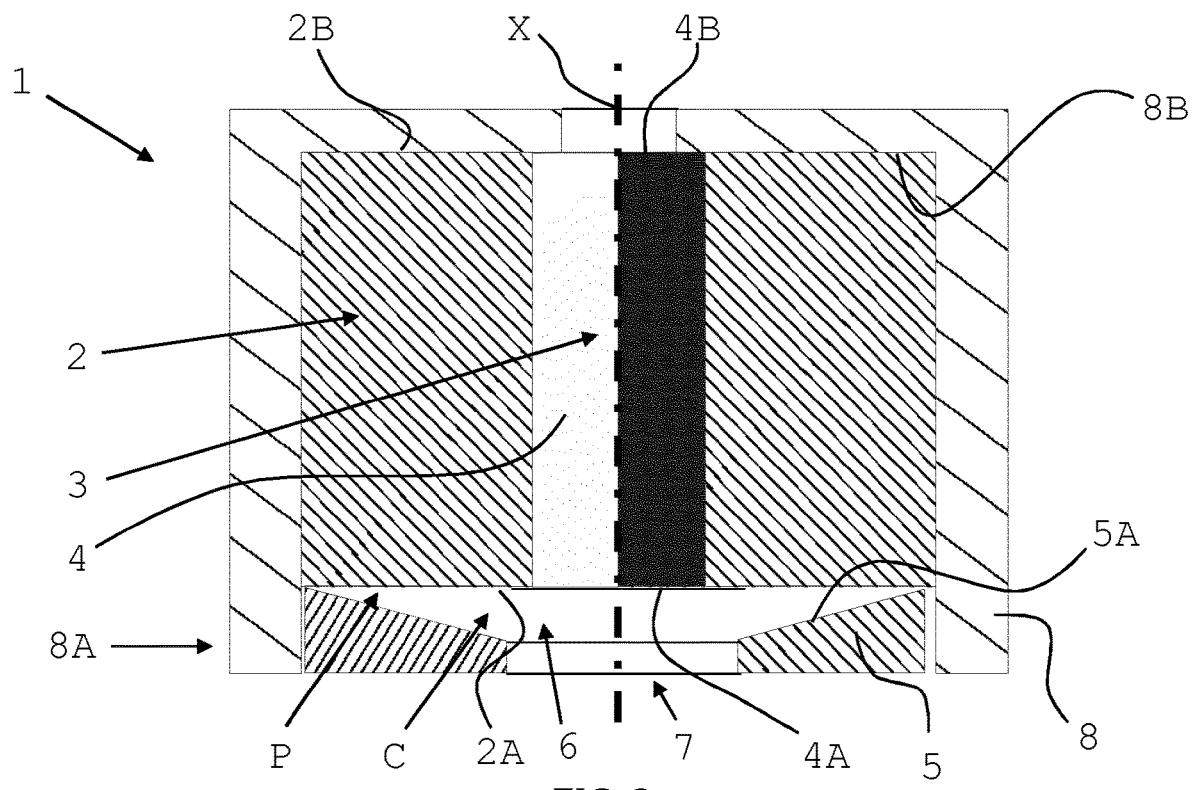
FIG. 2 shows a schematic cross sectional view of a nozzle fixing according to the invention.

In FIG. 2, a schematic cross sectional view of a nozzle fixing assembly 1 according to the invention is shown. Contrary to the assembly of FIG. 1, the high pressure side 2A of seal element 2 is substantially flat, i.e. it lies in a plane being perpendicular to longitudinal axis X of seal element 2. Further, high pressure side 5A of pressure element 5 is chamfered in a way that, in the depicted assembled state, the distance between these high pressure sides 2A, 5A is higher in a central region C than in a peripheral region P. The distance is measured parallel to the direction of longitudinal axis X.

The depicted embodiment further comprises a pot shaped holder 8 which has a recess. Inside this recess, seal element 2 with nozzle body 4 and pressure element 5 are arranged. Holder 8 comprises a low pressure surface 8B which is in contact with the (low pressure) outlet side 4B of nozzle 4. To minimize the gap surrounding seal element 2 that must be sealed as well, holder 8 has an inside contour matching the outside contour of seal element 2. At its high pressure end 8A, holder 8 contains entire pressure element 5 with its high pressure side 5A.

As can be seen, high pressure side 5A of pressure element 5 is only in minor physical contact with the high pressure side 2A of the seal element 2 at the outside of periphery P. Thus, pressure element 2 secures seal element 2 in its position. Also, if pressure element 2 is pushed further into the recess (not shown), permanent physical pressure is exerted onto seal element 2, resulting in a deformation thereof (not depicted). But even without any significant physical contact, when a pressure pulse enters space 6, said pulse is becoming more concentrated the farther it travels to the periphery P. Hence, at the periphery P, stronger pressure is exerted than in the center C, temporarily resulting in said deformation again.

In both cases, the deformation is such that the walls of continuous opening 3 that touch nozzle body 4 are (permanently or temporarily) moved against said body, sealing it against liquid that otherwise might bypass the interior channels of nozzle body 4.

As can be seen, in the present example, in the depicted cross section which runs along longitudinal axis X, the chamfered surface has a linear shape or profile. However, other profiles are possible as well (not depicted). The effect is maintained as long the rule that the space must be shallower at the periphery than in the center is followed. In the example, the high pressure side 5A of pressure element 5 is chamfered substantially in its entirety.

If the outer wall of the holder 8 has a thread (not shown), it can be screwed into a matching thread (not shown) of holder 8, such that pressure element 5 serves as a closure of the holder's 8 high pressure end 8A.

Figure 3:
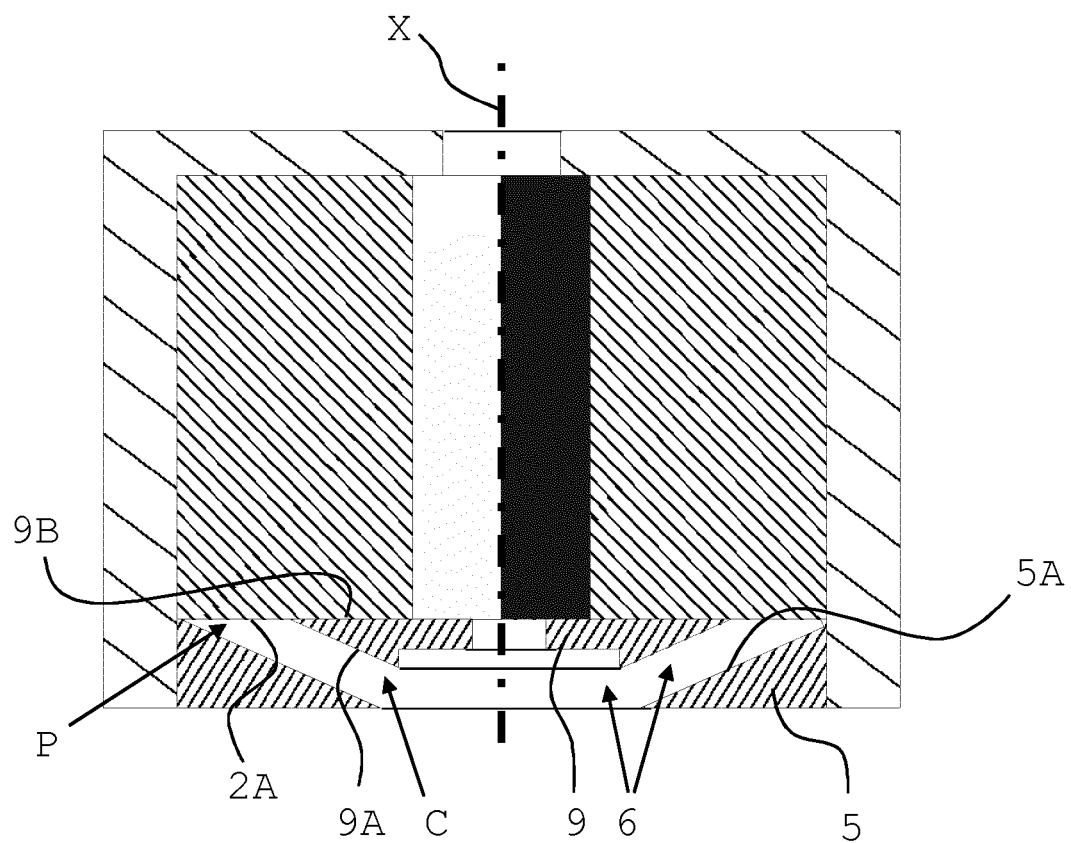
FIG. 3 shows a schematic cross sectional view of another nozzle fixing according to the invention.

FIG. 3 shows a further example of a nozzle assembly 1, comprising an optional washer 8. Not all reference numerals are given in this figure.

The washer 9 is arranged between the two high pressure sides 2A, 5A of seal element 2 and pressure element 5, respectively. The washer 9 has one continuous opening (no reference numeral) for fluidic connection of space 6 and nozzle body 4.

A first side 9B for contacting the high pressure side 2A of the seal element 2 is substantially flat.

An opposite second side 9A which faces the high pressure side 5A of the pressure element 5 is chamfered in a way that the distance between second side 9A and high pressure side 2A of seal element 2 is higher in a central region C than in a peripheral region P. Therefore, an interspace is provided between second side 9A of washer 8 and high pressure side 5A of pressure element 5. The interspace is more narrow in its periphery P than in its center C. Thus, the aforementioned pressure concentration effect is maintained.

As can be seen, second surface 9A of washer 9 has a profile resembling the negative of the profile of the chamfered surface of pressure element 5. However, other profile combinations are possible as well, e.g. such combinations where the aforesaid distance is greater in the center, and/or smaller in the periphery than in the depicted example.

LIST OF REFERENCES 1, 1' nozzle fixing assembly
2 seal element 2A high pressure side
2B outlet side
3 continuous opening
4 nozzle body
4A high pressure side
4B outlet side
5 pressure element
5A high pressure side
6 space
7 central opening
8 holder
8A high pressure end
8B low pressure surface
9 washer
9A second side
9B first side
X longitudinal axis
C central region, center
P peripheral region, periphery

What is claimed is:

1. A medical inhaler or a nebulizer for medical fluids comprising a nozzle fixing assembly, the nozzle fixing assembly configured to be substantially pressure tight when a nozzle body is inserted, comprising:
   an elastically deformable seal element, having a continuous opening configured to receive a nozzle body, said seal element and said nozzle body each having a high-pressure side and an outlet side;
   a pressure element with a high-pressure side, said side being arranged to face the high-pressure side of the seal element;
   wherein
   (i) the high-pressure side of the seal element is substantially flat and lies in a plane being perpendicular to a longitudinal axis of the seal element, wherein said longitudinal axis follows said continuous opening, and
   (ii) the high-pressure side of the pressure element comprises a central region with a central opening and a peripheral region surrounding the central region and encompassing an outer perimeter of the high-pressure side of the pressure element, the high-pressure side of the pressure element being inclined or sloped in a way that, in the assembled state, the distance between a surface of the high-pressure side of the pressure element and the high-pressure side of the seal element decreases from the central opening to the outer perimeter, wherein said central region is a region facing said continuous opening when following said longitudinal axis.

2. The medical inhaler or the nebulizer for medical fluids comprising the nozzle fixing assembly according to claim 1, additionally comprising the nozzle body, wherein the nozzle body is inserted in the continuous opening.

3. The medical inhaler or the nebulizer for medical fluids comprising the nozzle fixing assembly according to claim 1, further comprising a holder with a recess, inside which the seal element and the pressure element are arranged, the holder comprising (i) a low pressure surface which is, in the assembled state, in contact with the outlet side of the nozzle body, and (ii) an inside contour matching an outside contour of the seal element, and (iii) a high-pressure end, containing at least the high-pressure side of the pressure element.

4. The medical inhaler or the nebulizer for medical fluids comprising the nozzle fixing assembly according to claim 1, wherein, in the assembled state, the high-pressure side of the pressure element is at least partially in physical contact with the high-pressure side of the seal element.

5. The medical inhaler or the nebulizer for medical fluids comprising the nozzle fixing assembly according to claim 1, wherein said distance is, in the assembled state, zero at the peripheral region, and larger than zero at the central region.

6. The medical inhaler or the nebulizer for medical fluids comprising the nozzle fixing assembly according to claim 1, wherein, in a cross section along said longitudinal axis, the inclined or sloped surface of the pressure element has a linear, a concave, or a convex profile.

7. The medical inhaler or the nebulizer for medical fluids comprising the nozzle fixing assembly according to claim 1, wherein the high-pressure side of the pressure element has a central region which is substantially flat and parallel to the high-pressure side of the seal element.

8. The medical inhaler or the nebulizer for medical fluids comprising the nozzle fixing assembly according to claim 1, wherein in the assembled state the pressure element serves as a closure of the holder's high-pressure end, or wherein a lid is provided which can be attached to said high-pressure end.

9. The medical inhaler or the nebulizer for medical fluids comprising the nozzle fixing assembly according to claim 1, wherein the high-pressure side of the pressure element is inclined or sloped substantially in its entirety.

10. The medical inhaler or the nebulizer for medical fluids comprising the nozzle fixing assembly according to claim 1, further comprising a washer which is arranged between the two high-pressure sides of the seal element and the pressure element, wherein the washer has
    a first side for contacting the high-pressure side of the seal element, said first side being substantially flat,
    an opposite second side which faces the high-pressure side of the pressure element, and
    the washer having a continuous opening for fluidic connection to the nozzle body through the washer from the second side to the first side,
wherein
    the high-pressure side of the seal element comprises a central region and a peripheral region encompassing an outer perimeter of the high-pressure side of the seal element,
    said second side is inclined or sloped in a way that, in the assembled state, the distance between said second side and the high-pressure side of the seal element is greater in the central region of the high-pressure side of the seal element than in the peripheral region of the high-pressure side of the seal element, and
    an interspace is provided between the second side of the washer and the high-pressure side of the pressure element.

11. The medical inhaler or the nebulizer for medical fluids comprising the nozzle fixing assembly according to claim 10, wherein said interspace is more narrow in its periphery than in its center.

12. The medical inhaler or the nebulizer for medical fluids comprising the nozzle fixing assembly according to claim 10, wherein, in a cross section along said longitudinal axis, the second side of the washer has a profile resembling the negative of the profile of the inclined or sloped surface of the pressure element.

* * * * *